(12) United States Patent
Strauss et al.

(10) Patent No.: US 6,899,307 B2
(45) Date of Patent: May 31, 2005

(54) CARRIER SYSTEM FOR A MEDICAL APPARATUS

(75) Inventors: Wolfgang Strauss, Staig (DE); Franz Krug, Aalen (DE); Fritz Zimmermann, Essingen (DE); Alfons Abele, Schwäbisch Gmünd (DE); Maren Lehmann, Oberkochen (DE); Lauric Weber, Aalen (DE)

(73) Assignee: Carl-Zeiss-Stiftung, Heidenheim (DE)

( * ) Notice: Subject to any disclaimer, the term of this patent is extended or adjusted under 35 U.S.C. 154(b) by 0 days.

(21) Appl. No.: 10/440,270

(22) Filed: May 19, 2003

(65) Prior Publication Data

US 2003/0230698 A1 Dec. 18, 2003

(30) Foreign Application Priority Data

May 18, 2002 (DE) ......................................... 102 22 337
Jan. 10, 2003 (DE) ......................................... 103 00 620

(51) Int. Cl.[7] .............................................. F16M 11/04
(52) U.S. Cl. .............................. 248/280.11; 248/123.11
(58) Field of Search ........................... 248/274.1, 276.1, 248/278.1, 280.11, 292.11, 122.1, 123.11, 123.2, 124.1; 396/428; 312/223.6

(56) References Cited

U.S. PATENT DOCUMENTS

| 3,072,374 A | * | 1/1963 | Bodian ..................... 248/278.1 |
| 4,494,177 A | * | 1/1985 | Matthews ................... 362/402 |
| 4,523,732 A | * | 6/1985 | Biber et al. ............ 248/123.11 |
| 4,770,384 A | * | 9/1988 | Kuwazima et al. ..... 248/281.11 |
| 5,014,693 A | * | 5/1991 | Wright et al. .......... 128/204.18 |
| 5,240,220 A | * | 8/1993 | Elberbaum ................... 248/558 |
| 5,380,219 A | | 1/1995 | Klier .......................... 439/446 |
| 5,425,069 A | * | 6/1995 | Pellegrino et al. .......... 378/198 |
| 5,609,316 A | * | 3/1997 | Tigliev .................... 248/123.11 |
| 5,611,513 A | * | 3/1997 | Rosen .................... 248/222.11 |
| 6,328,458 B1 | * | 12/2001 | Bell et al. .................... 362/371 |
| 6,364,268 B1 | * | 4/2002 | Metelski ..................... 248/317 |
| 6,491,273 B2 | * | 12/2002 | King et al. ............... 248/276.1 |
| 6,736,364 B2 | * | 5/2004 | Oddsen, Jr. ................. 248/585 |

FOREIGN PATENT DOCUMENTS

DE 2643780 3/1978

OTHER PUBLICATIONS

Information sheet of Carl Zeiss entitled "Effizienz und Bedienungsfreundlichkeit—Das Bodenstativ NC4", Jun. 2002.

* cited by examiner

*Primary Examiner*—Anita King
*Assistant Examiner*—Jon Szumny
(74) *Attorney, Agent, or Firm*—Walter Ottesen

(57) ABSTRACT

A carrier system (10) for a medical apparatus (11) is disclosed. The carrier system includes rotation joints (17, 18, 20). A supply line harness runs in the carrier system (10) and is run so that it is covered. The rotation joint (18) includes a tube-shaped holding member on which fingers are formed which hold a rotation joint. A joint element, which is rotatably journalled in a joint receptacle, is provided in the rotation joint (20). The joint element has a wave-shaped section which is connected via a connecting section to an annularly-shaped section functioning to accommodate a connecting arm.

7 Claims, 13 Drawing Sheets

CARRIER SYSTEM FOR A MEDICAL APPARATUS

BACKGROUND OF THE INVENTION

A support system for a medical apparatus is, for example, manufactured by Carl Zeiss of Oberkochen, Germany, under the product designation "NC-4-Floor Stand" and "NC-4-Ceiling System". Corresponding support systems are also offered by the Leica Company under the product designation "OHS-1 Floor Stand". The Altvic Italia Company likewise offers such support systems for sale. These support systems have several linkage arms which, for example, support a surgical microscope. Wiring harnesses are mounted on these linkages which supply the surgical microscope with electrical energy and make possible the transmission of data with a video system. Also, these wiring harnesses can be in the form of light conductors and make available illuminating light for illuminating regions to be viewed.

German patent publication 2,643,780 discloses a tiltable floor lamp which includes a ball joint having a cable passthrough in the lamp base. A telescope tube arrangement is accommodated on this ball joint wherein a lamp cable is guided. Limiting pins and limiting bars are provided in the telescope tubes in order to avoid an excessive twisting of the telescope tubes relative to each other.

In U.S. Pat. No. 5,380,219, a ball joint is described which can be clamped tight by means of a cap nut and which is configured to have a cable passthrough. This ball joint is part of a connector.

Surgical microscopes utilized to carry out surgical procedures can hold the danger of a source of infection. For this reason, sterile drapes are usually pulled over the surgical microscopes for surgery. The drape ensures, on the one hand, a freedom of germs and, on the other hand, protects the surgical microscope against contamination. Surgical microscopes are increasingly used in dental work and in the area of ENT medical practice on an everyday basis. In this area of use, the requirements as to sterility and cleanliness of apparatus are not as high as in operating rooms. Nonetheless, an easy cleaning of apparatus and instruments which are utilized in this area is desirable.

Freely guided cables, recesses and projections on a support system can, however, be cleaned only with difficulty.

SUMMARY OF THE INVENTION

In view of the above, it is an object of the invention to provide a support system for a medical apparatus which can be easily cleaned and can be used for minor surgical procedures also without a sterile drape because a certain minimum sterility can be established in a simple manner such as by wiping down the apparatus.

The support system of the invention has at least one holding arm which has a joint unit connected on one carrier arm and a supply wire harness which runs on the holding arm and on the carrier arm. The joint unit has means for compensating for a load torque. The course of the supply wiring harness is covered from the holding arm to the carrier arm.

In this way, a guide for a cable harness is provided which avoids dangling cable loops to effect the operation of the apparatus.

According to another feature of the invention, means are provided for limiting rotation. In this way, an excessive twisting of a cable harness passing through the joint unit is prevented.

According to another feature of the invention, a cable passthrough channel is formed on the holding arm. In this way, a separation of the cable harness and the drive is made possible.

According to another feature of the invention, the cable guide channel is covered by a plastic strip. In this way, easy accessibility to a cable harness disposed in the carrier arm is ensured.

According to another feature of the invention, a guide slot is provided on the holding arm to guide the plastic strip. In this way, the plastic strip can be easily removed.

According to another feature of the invention, a first holding arm and a second holding arm are provided for accommodating a medical apparatus. The first holding arm is carried by the carrier arm and the second holding arm is configured as a connecting arm for the medical apparatus. In this way, the medical apparatus can be positioned in at least two degrees of freedom of movement.

According to another feature of the invention, the first holding arm and the second holding arm are connected by a joint unit to which means for compensating a torque load are assigned. In this way, a substantially force-free movement of the medical-optical apparatus is made possible.

According to still another feature of the invention, the second holding arm is configured to have an O-shape. In this way, a weight-saving assembly group with a high stability is provided for the carrier system.

According to another feature of the invention, a covering is provided in the joint unit for connecting the first holding arm to the second holding arm. In this way, excellent accessibility to the cable harness at the joint unit is ensured.

According to another feature of the invention, the joint unit is configured as a rotating joint which includes a joint element rotatably journalled in a joint receptacle. The joint element has a shaft section which is connected via a connecting section to an annularly-shaped section functioning to accommodate a connecting arm. In this way, a stable joint connection is provided which permits a cable harness to be guided therethrough while providing a weight-saving configuration.

According to another feature of the invention, bores are provided for rotation limiting members in the connecting section. These rotation limiting members effect a limiting of rotation via a stop lug configured in the joint receptacle. In this way, a desired limiting of rotation can be adjusted by setting rotation limiting members in bores.

In a further embodiment of the invention, the supply line harness is guided through the annularly-shaped section. In this way, a movement of a cable harness, which is guided through the rotation joint, is minimized when displacing the rotational joint.

According to another embodiment of a support system, a rotation joint is provided as a joint unit which includes a tube-shaped holding member on which one or several holding fingers are formed which hold the rotation bearing. In this way, a stable joint arrangement for a cable passthrough is provided which is built up with a savings with respect to weight.

In another embodiment of the invention, a shaft element is journalled on the rotation support and a tube-shaped sleeve piece is connected to the shaft element and is connected to the holding arm. In this way, a joint arrangement is provided having a surface which can be easily cleaned.

In a further embodiment of the invention, the tube-shaped holding member is connected to the carrier arm by a rotation joint. In this way, good maneuverability for medical-optical equipment is ensured which is accommodated on the carrier system.

In another embodiment of the invention, at least one joint unit is configured as a rotation joint having a cable passthrough. In this way, a covered cable passthrough through the entire carrier system is made possible.

According to still another feature of the invention, the means "compensation of a load torque" are configured as spring means. In this way, a force-free movement for medical-optical equipment is possible.

According to another feature of the invention, the spring means include a torsion spring. In this way, a space-saving configuration is made possible for a unit for compensation of a load torque.

In another embodiment of the invention, the spring means include a linear spring. In this way, a state of equilibrium can be precisely adjusted in a unit for rotational decoupling.

According to another feature of the invention, the carrier system includes at least one magnetic brake. In this way, a user-friendly locking of the carrier system is made possible.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
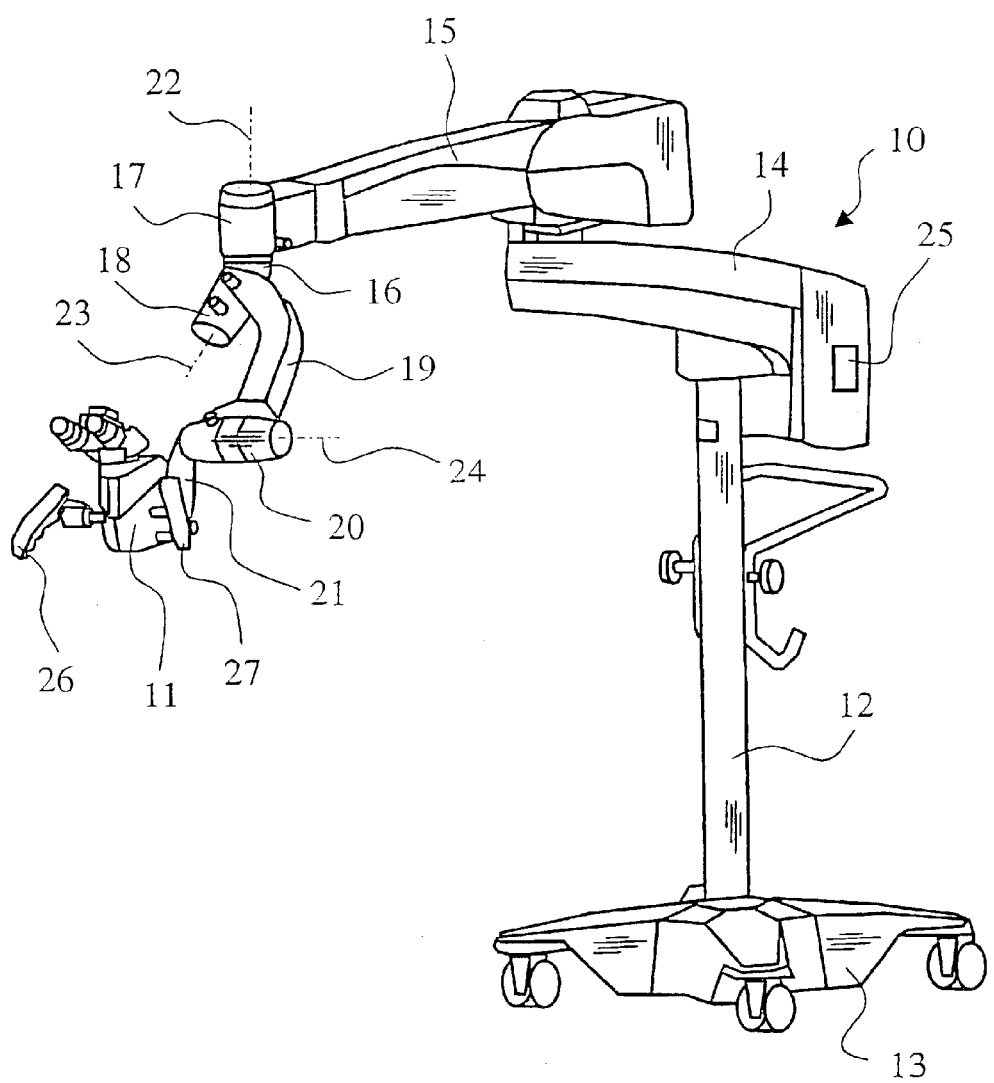
FIG. 1 is a perspective view of a carrier system shown with a surgical microscope.

FIG. 1 shows a carrier system 10 for a medical apparatus on which a surgical microscope 11 is accommodated. The carrier system 10 is configured as a stand unit 10 and the stand unit includes a stand column 12 which is held by a movable base 13. A first carrier arm 14 is accommodated on the stand column 12 so as to be rotationally movable. This first carrier arm 14 carries a second carrier arm 15 on which a carrier member 16 is journalled in a rotation joint 17. The surgical microscope 11 with a first holding arm 19 is accommodated on the carrier member 16 via a joint unit 18 configured as a rotation joint. The holding arm 19 is connected to a second holding arm 21 via a joint unit 20 configured as a rotation joint. The second holding arm 21 functions as a connecting arm for taking up the surgical microscope 11.

The rotation joint 17 makes possible a rotational movement of the surgical microscope 11 about an axis 22 which is at an angle to a rotational axis of the rotation joint 18. This rotation axis is identified by reference numeral 23. The joint unit 20 makes possible a rotational movement of the surgical microscope 11 about an axis 24.

The surgical microscope 11 is rigidly connected to the second holding arm 21.

The carrier system 10 includes a supply module 25 wherein an illumination unit is mounted. Further, connectors for a video cable and for connecting to a house power supply are provided in the supply module.

A harness of supply lines is guided from the supply module 25 to the surgical microscope 11. This harness of supply lines includes light conductors as well as electric cables for the drive motors of a zoom assembly and for a video unit integrated into the surgical microscope 11. The harness of supply lines is not visible in FIG. 1. This harness runs in a cable guide channel which is not less than 30 mm at any cross section.

Handles 26 and 27 are formed on the surgical microscope 11 with which the surgical microscope 11 can be moved. The surgical microscope is accommodated on the carrier system 10. Operator-controlled elements are provided on the handles 26 and 27 for actuating the microscope control functions.

Means for compensating a load torque are assigned to the joint units 18 and 20. The load torque is caused by the weight of the surgical microscope and the corresponding mass distribution of the holding elements in the rotational axes 23 and 24.

Figure 2:
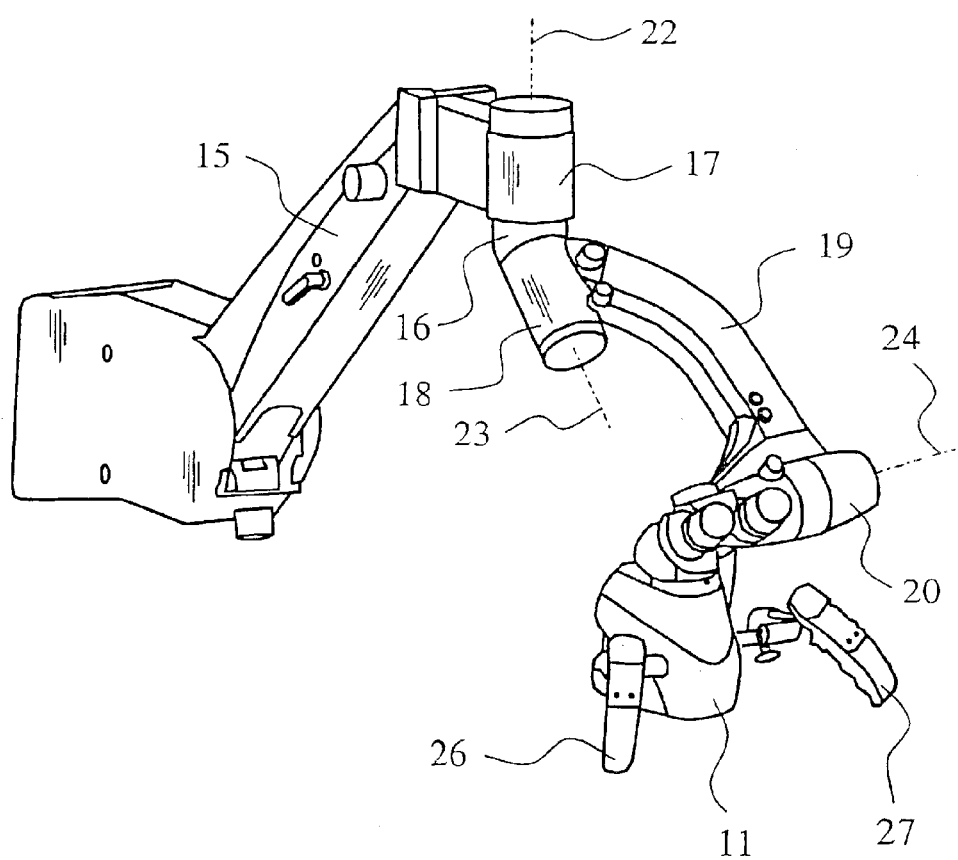
FIG. 2 is a detailed perspective view of a carrier system supporting a surgical microscope.
Figure 3:
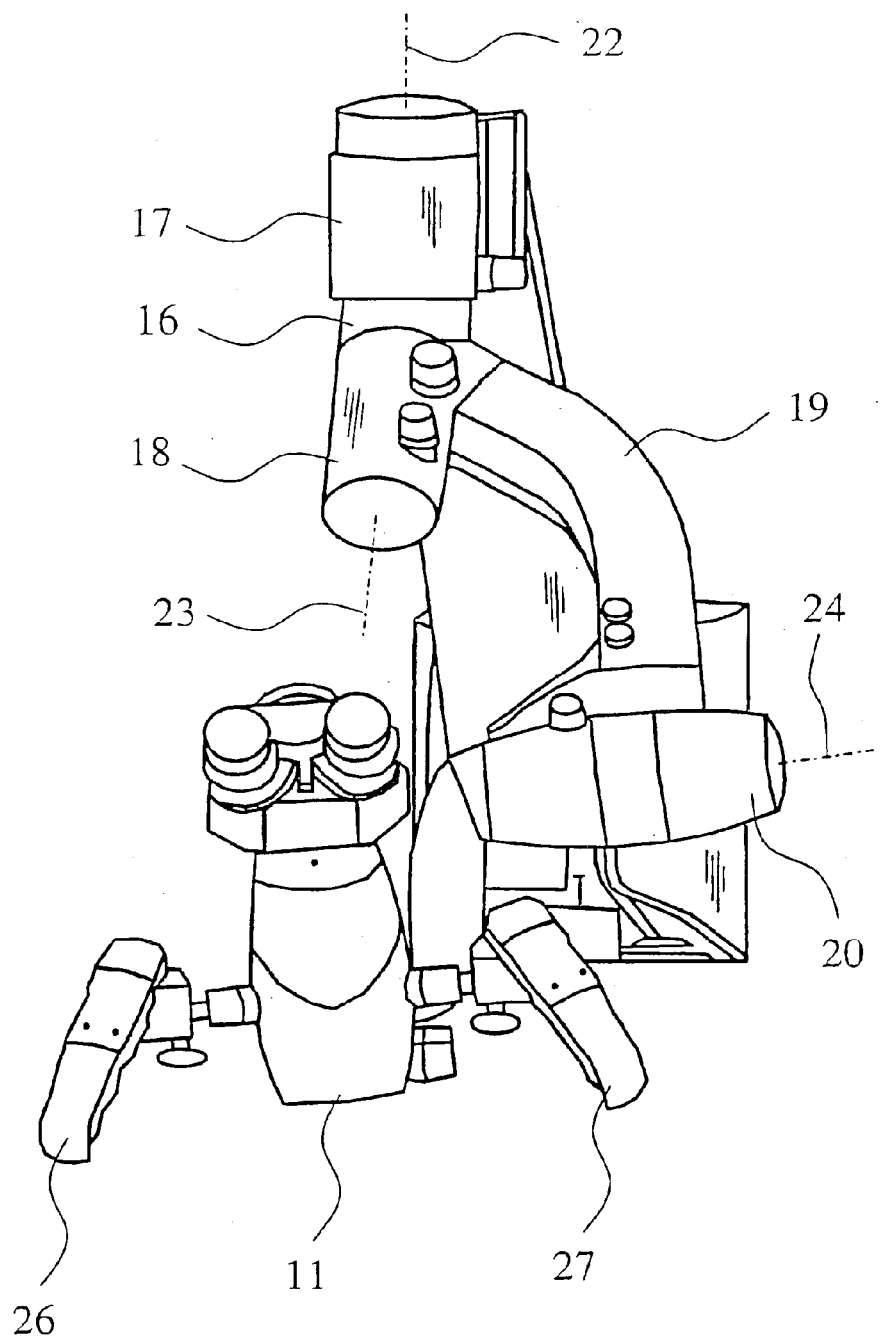
FIG. 3 is a further perspective detailed view of a carrier system with a surgical microscope.

FIGS. 2 and 3 show a part view of the carrier system with the surgical microscope of FIG. 1 as seen at different viewing angles. The component assemblies in FIGS. 2 and 3 are identified by the same reference numerals as in FIG. 1 to the extent that they are visible.

Figure 4:
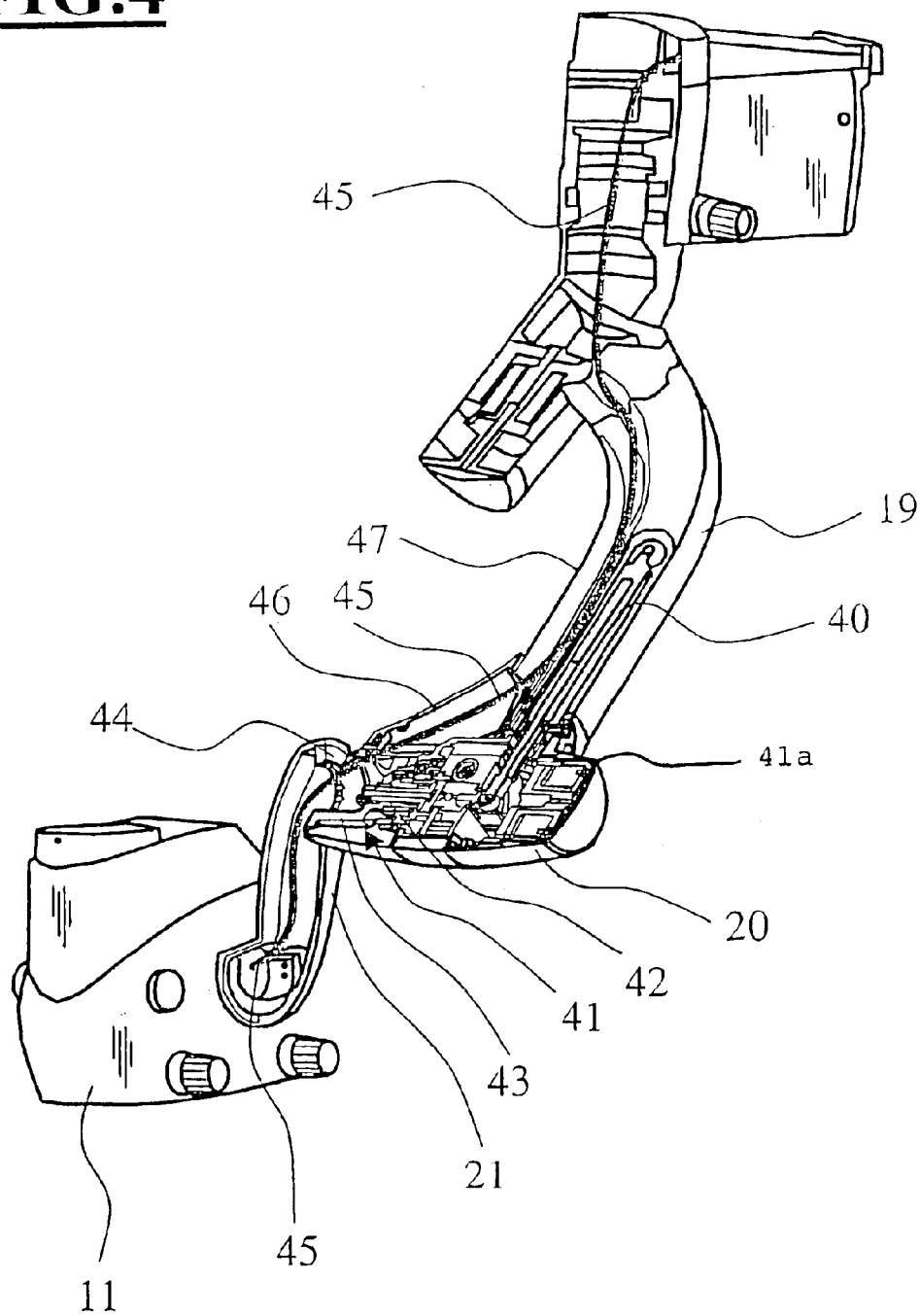
FIG. 4 is a three-dimensional perspective section view of the carrier system of FIG. 2.

FIG. 4 shows a perspective section view of a part of the carrier system with the surgical microscope of FIG. 1. Insofar as the component assemblies correspond to each other, they are, in turn, provided with the reference numerals used in the description of the above FIGS. 1, 2 and 3.

The joint unit 20 is provided with a gas-pressure spring 40 as a mechanism for compensating a load torque in the joint unit 20. The gas-pressure spring 40 is supported by the holding arm 19. A movement of the joint unit 20 can be prevented by a magnetic brake 41a. The joint unit 20 includes a rotatably journalled joint element 41 which is operatively connected to the gas-pressure spring 40. The joint element 41 has a shaft section 42 which is connected to an annularly-shaped section 44 via a connecting section 43. The annularly-shaped section 44 serves to accommodate the holding arm 21.

The holding arm 21 is configured to have a tubular shape and surrounds the harness of supply lines 45. The harness is guided through the carrier arms and the holding arms of the carrier system from the supply module 25 to the surgical microscope 11. The harness of supply lines 45 runs through the annularly-shaped section 44 of the joint element 41 and is guided into the holding arm 19 covered by a cover part 46. The cover part 46 is attached by only one screw to the joint unit 20. A plastic strip 47 is provided on the holding arm 19 and runs in a corresponding guide slot. When the cover unit 46 is removed, then the plastic strip 47 can be pulled from the guide slot. The harness of supply lines 45, which runs in the holding arm 19, is then accessible.

Figure 5:
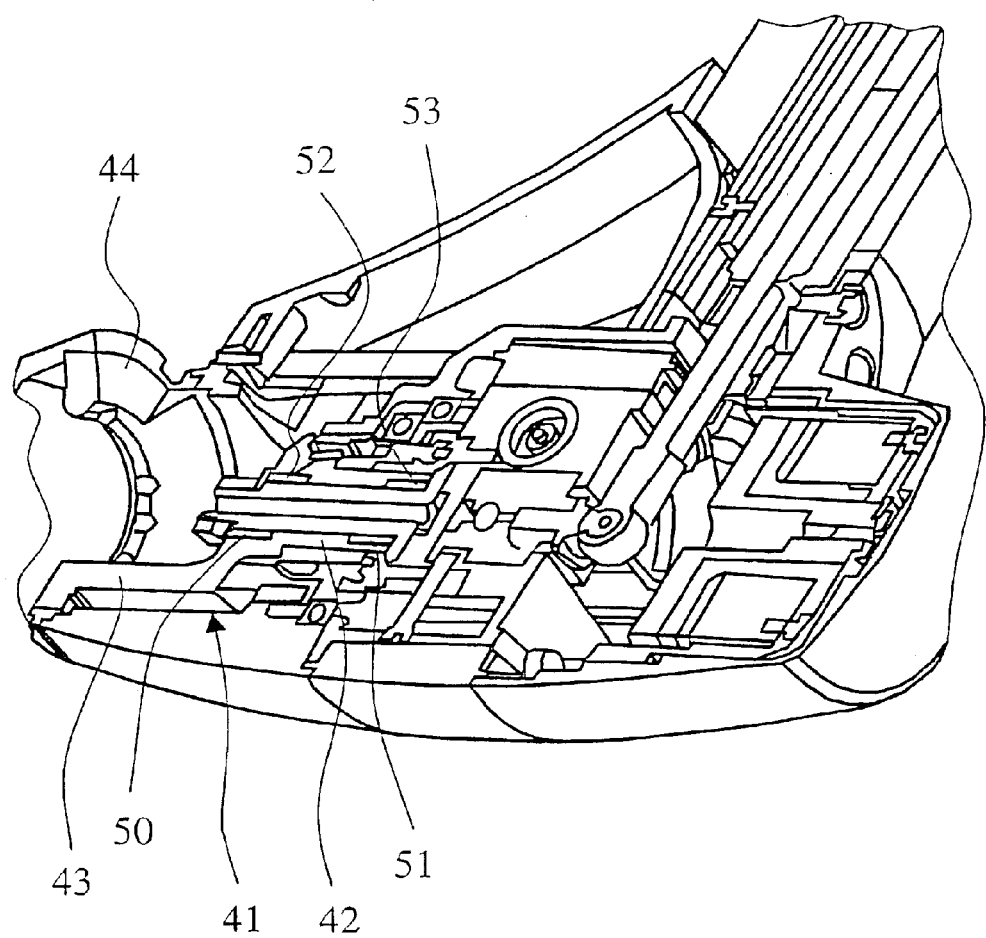
FIG. 5 is a perspective section view of a joint unit of the carrier system.

FIG. 5 shows an enlarged view of the joint unit 20 in a perspective section. The shaft section 42 of the joint element 41 is configured as a hollow shaft and is journalled on needle bearings (50, 51, 52, 53). Insofar as the components are visible in FIG. 5 and are described with respect to the previous figures, they are provided here with the same reference numerals as in these previous figures.

Figure 6:
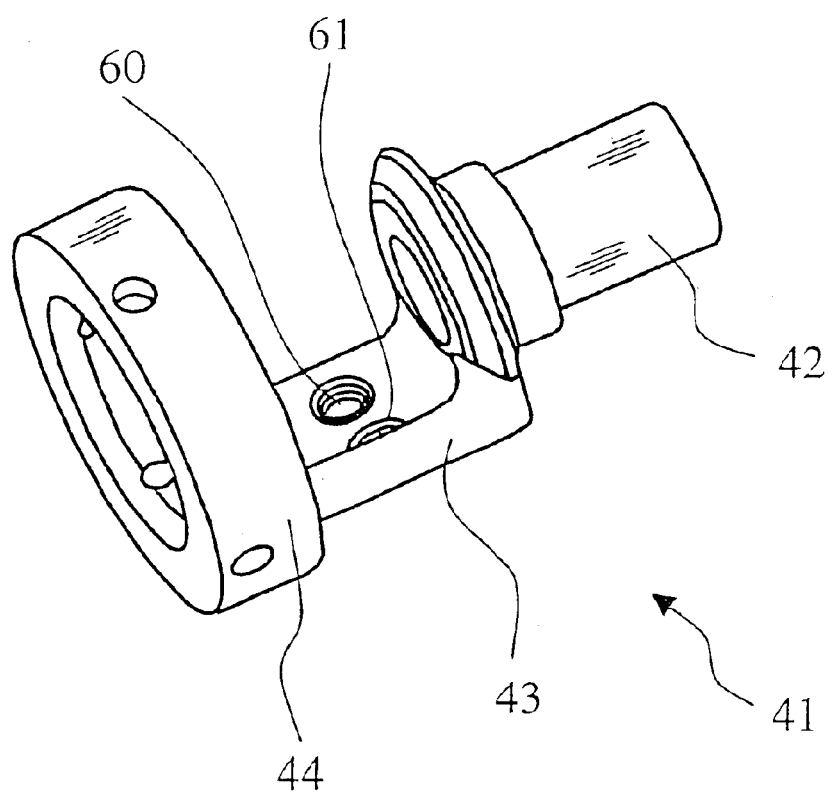
FIG. 6 is a component assembly of the joint unit of FIG. 5.

FIG. 6 shows a joint unit 41 on which bores 60 and 61 are provided at the connecting section 43. Screws can be placed in the bores 60 and 61 as rotation limiting members in order to form a mechanism for limiting rotation by coacting with corresponding projections on a receptacle for the joint element in the joint unit 20. A specific angular range can be fixed corresponding to which the joint unit 20 can be shifted by placing a screw either in the bore 60 or in bore 61. This prevents excessive twisting of the harness of supply cables when the joint unit 20 is moved.

Figure 7:
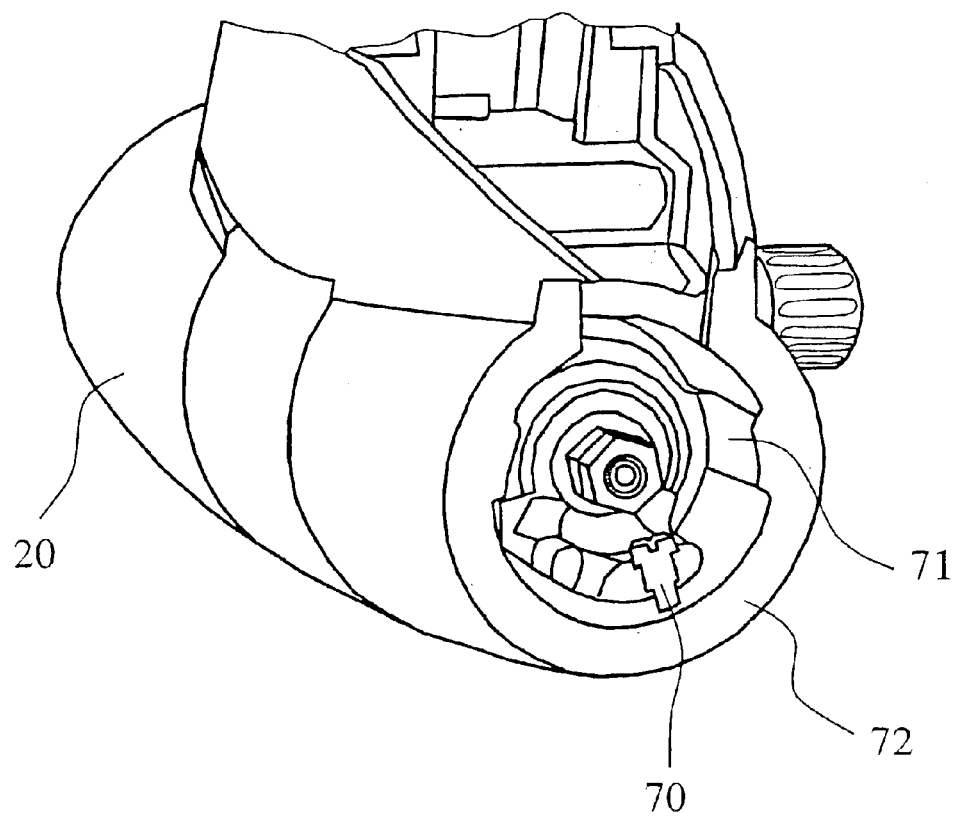
FIG. 7 is a further perspective view of the joint unit of FIG. 5.

FIG. 7 shows a section view of the joint unit 20 wherein a screw 70 for limiting rotation and a corresponding stop lug 71 on the housing 72 of the joint unit 20 can be seen.

Figure 8:
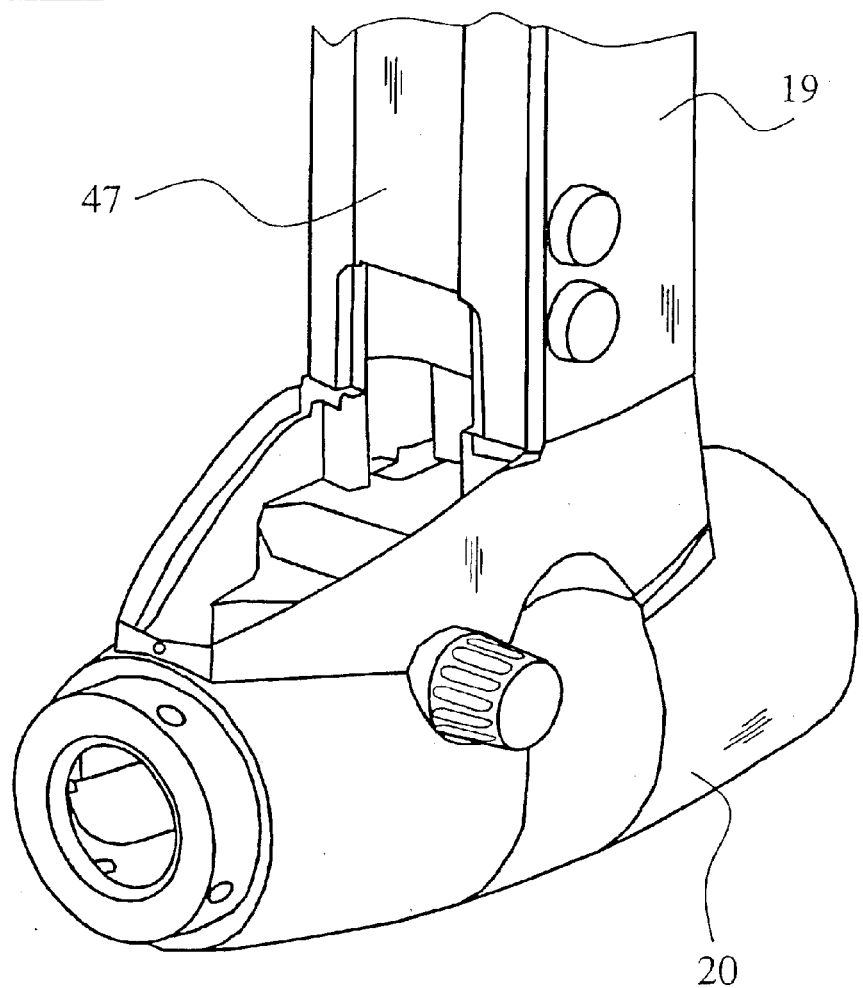
FIG. 8 is a further perspective view of the joint unit of FIG. 5.

The connecting region between the joint unit 20 and the holding arm 19 is shown in FIG. 8. A cutout is provided on the holding arm 19 in order to easily remove the plastic strip 47.

Figure 9:
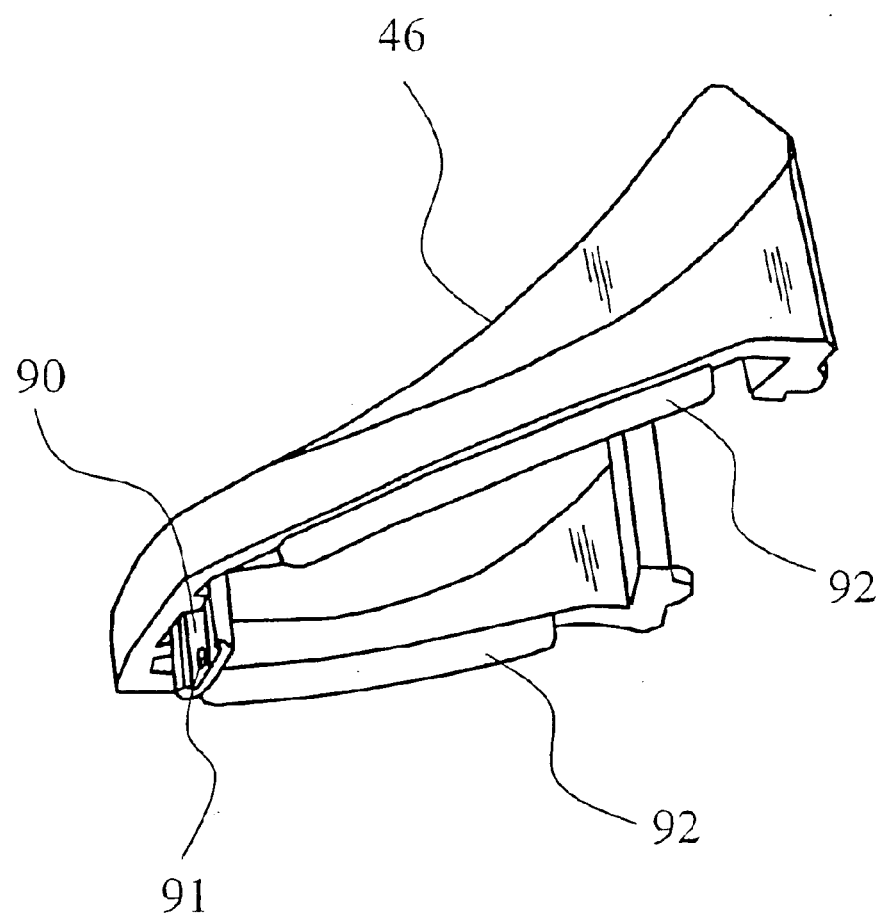
FIG. 9 is a perspective view of a covering for the joint unit of FIG. 5.

FIG. 9 shows the cover unit 46 of FIG. 5 in an enlarged view. The cover unit 46 has a seat 90 having a bore 91 for a screw as well as holding lamellae 92 which make possible a stable attachment of the cover unit 46 to the housing of the joint unit 20.

Figure 10:
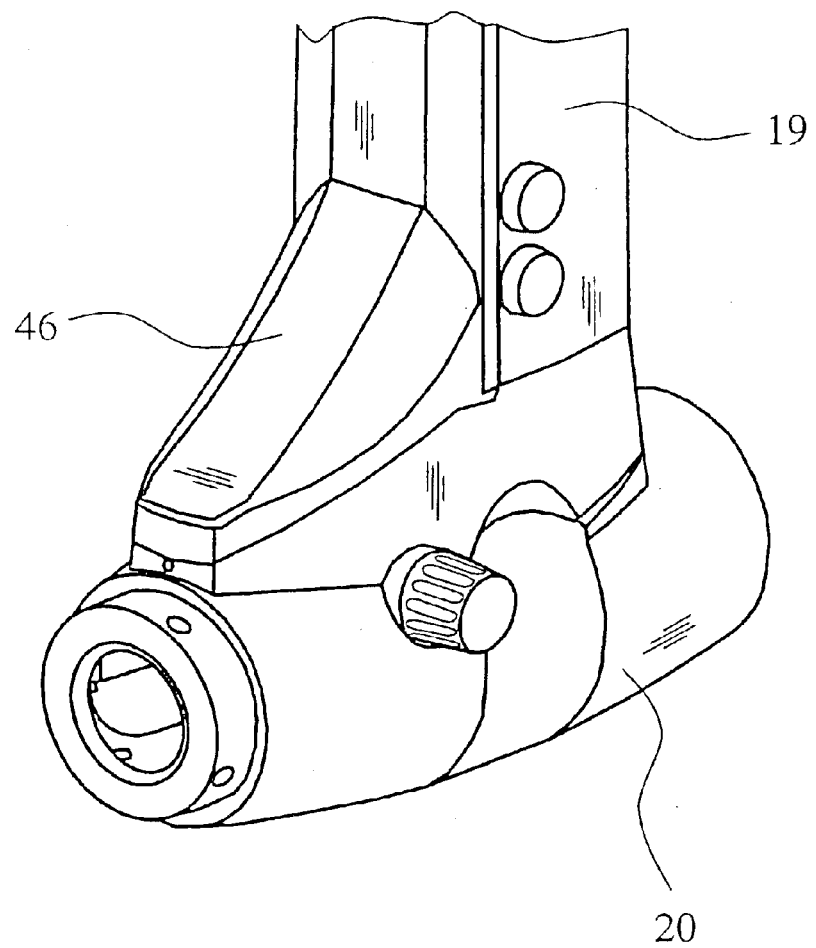
FIG. 10 is a perspective view of a section of a holding arm of the carrier system with the joint unit of FIG. 5.

As shown in FIG. 10, the outer contour of the cover unit 46 is rounded and configured so that a surface results which can be easily cleaned at the transition from the holding arm 21 of FIG. 1 to the holding arm 19 and the rotation joint 20. The surgical microscope 11 is connected to the holding arm 21.

Figure 11:
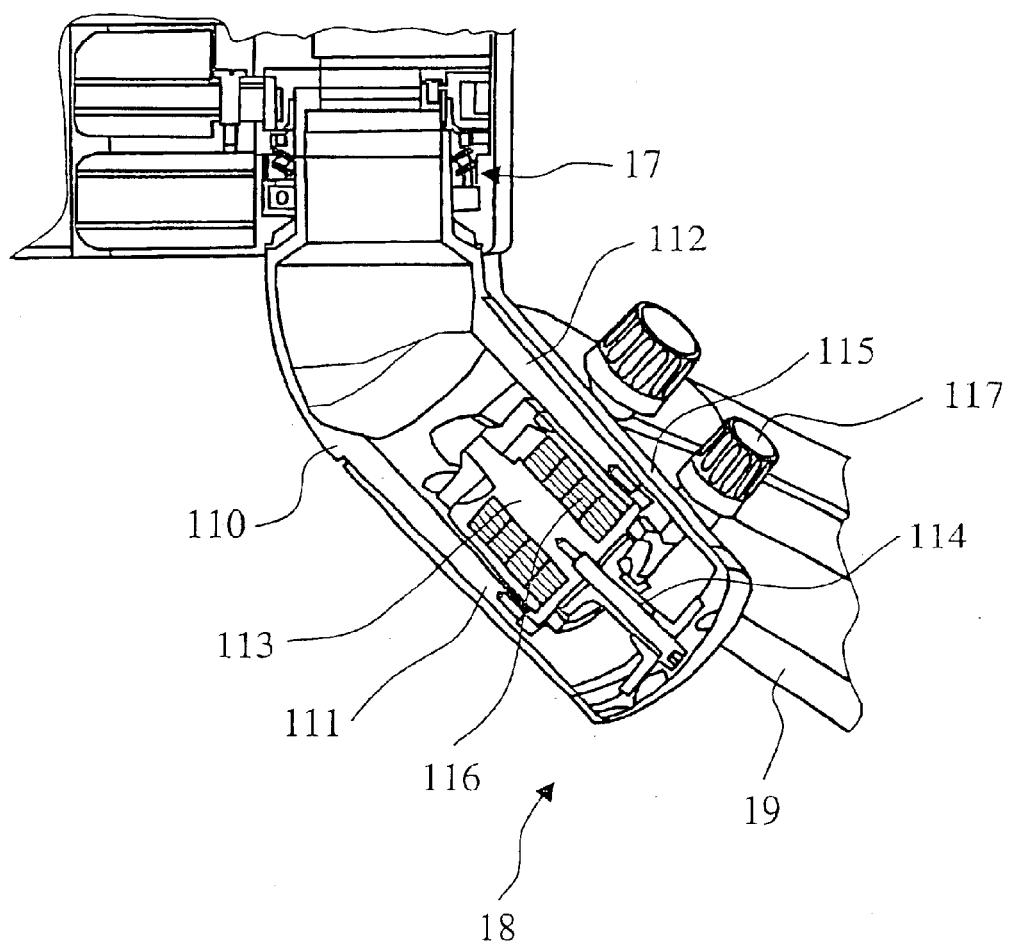
FIG. 11 is a further section view of a holding arm of the carrier system having a joint unit; and, FIGS. 12 to 14 show an assembly of components of the joint unit of FIG. 11.

FIG. 11 is an enlarged view of the joint unit 18 of FIG. 1. The joint unit 18 has a tube-shaped holding member 110 which is held in the rotation joint 17. Holding fingers 111 and 112 are formed on the tube-shaped holding member. These holding fingers 111 and 112 hold a rotation joint 113. In this rotation joint 113, a shaft element 114 is journalled to which a tube-shaped sleeve piece 115 is connected. This tube-shaped sleeve piece 115 is connected to the holding arm 19. A torsion spring 116 is provided in the joint unit 18 as a means for compensating a load torque. The joint unit 18 further includes an adjusting screw 117 by means of which the friction force can be adjusted which acts on the shaft element 114. By actuating the adjusting screw 117, a rotation of the joint unit 18 can be prevented.

Figure 12:
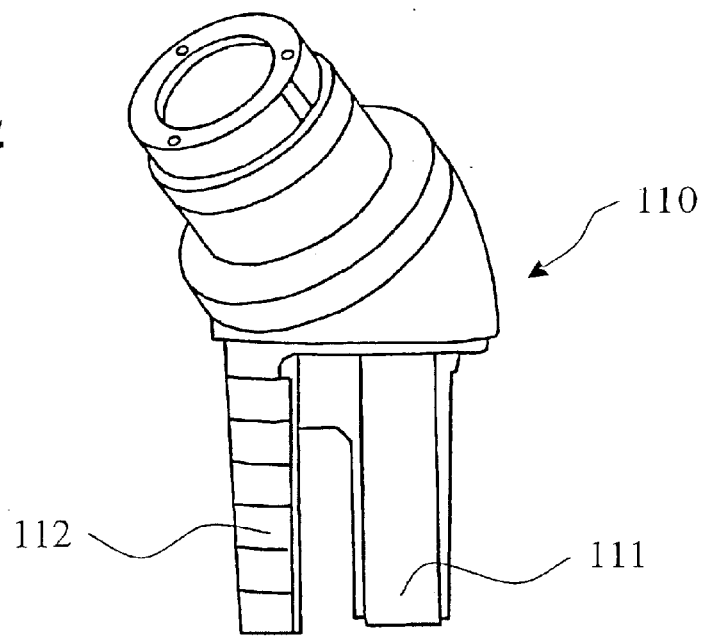
Figure 13:
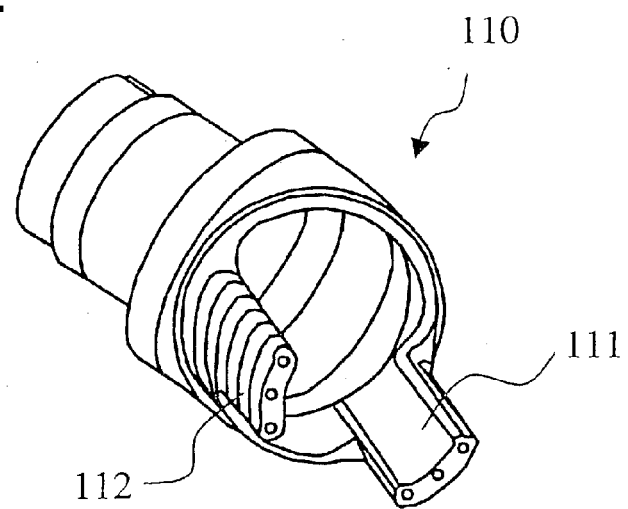
Figure 14:
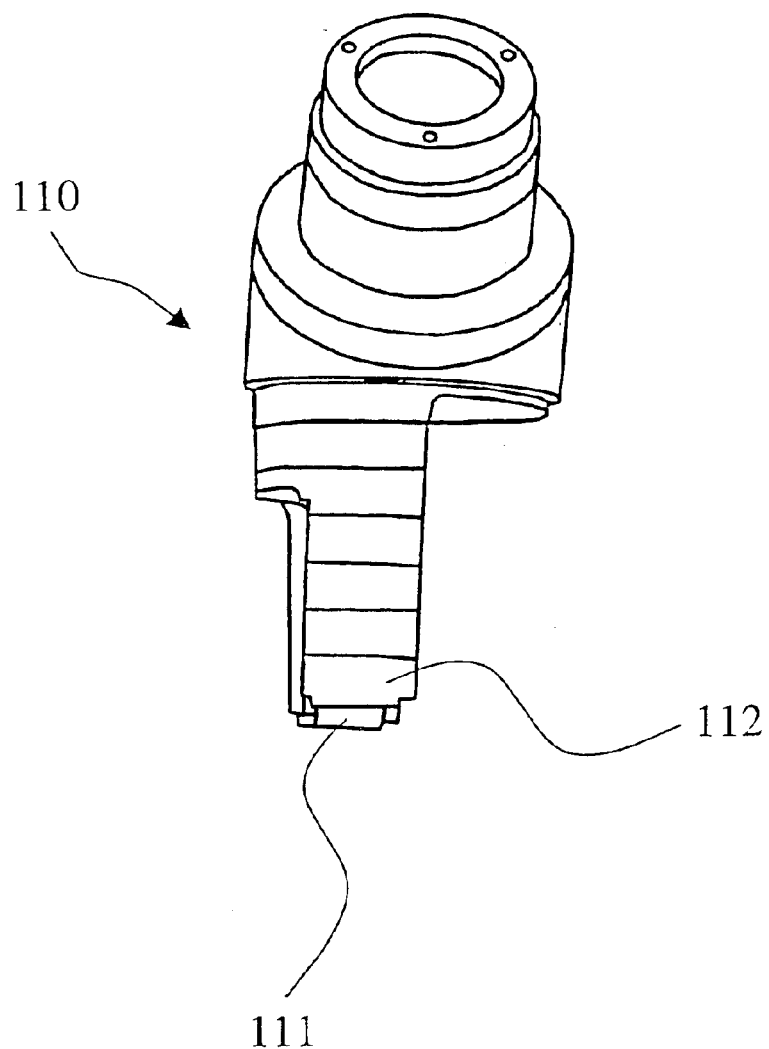

FIGS. 12, 13 and 14 show the tube-shaped holding member 110 in respectively different angular views.

Gaps having a width of approximately 1 mm are provided between the component assemblies of the carrier system which are movable relative to each other. In this way, a good movability of the carrier system is guaranteed also in the case of component tolerances. The surfaces of the component assembly are resistant to scratches and wiping. The surface is defined by a material which cannot be attacked by disinfectant agents.

Any other desired apparatus can be accommodated on the carrier system in lieu of a surgical microscope.

It is understood that the foregoing description is that of the preferred embodiments of the invention and that various changes and modifications may be made thereto without departing from the spirit and scope of the invention as defined in the appended claims.

What is claimed is:

1. A carrier system for a medical apparatus, the carrier system comprising:

a first holding arm adapted to be operatively connected to the medical apparatus;

a carrier arm;

a joint unit for connecting said first holding arm to said carrier arm;

said joint unit including means for compensating for a load torque;

a supply wiring harness adapted to be connected to said medical apparatus;

said first holding arm, said carrier arm and said joint unit conjointly defining an enclosed path for accommodating said supply wiring harness therein;

wherein said first holding arm is supported by said carrier arm; and, said carrier system further comprises a second holding arm for receiving the medical apparatus thereon and wherein said second holding arm is connected to said first holding arm;

wherein said joint unit is a first joint unit and said carrier system further comprises a second joint unit for connecting said second holding arm to said first holding arm; and, said second joint unit includes means for compensating for a load torque, and wherein said second joint unit is a rotational joint including a joint receptacle and a joint element rotatably journalled in said joint receptacle; and, said joint element further includes a shaft section and an annularly-shaped section for accommodating a connecting arm and a connecting section for connecting said annularly-shaped section to said shaft section.

2. The carrier system of claim 1, wherein said connecting section includes: bores; rotation limiting members for placement in said bores; and, stop lugs formed in said joint receptacle for coacting with said rotation limiting members to effect a limiting of rotation.

3. The carrier system of claim 2, wherein said first joint unit is a rotation joint including a tubularly-shaped holding member having at least one holding finger formed thereon and a rotational bearing held by said finger.

4. The carrier system of claim 3, said rotation joint further including a shaft element journalled in said rotational bearing and a tubularly-shaped sleeve connected to said shaft element; and, said first holding arm being connected to said tubularly-shaped sleeve.

5. The carrier system of claim 4, said tubularly-shaped holding member being connected to said carrier arm by means of a rotation joint.

6. The carrier system of claim 1, wherein said enclosed path includes a segment through said annularly-shaped section for guiding said supply wire harness therein.

7. The carrier system of claim 1, wherein at least one of said joint units is configured as a rotational joint having a cable passthrough.

* * * * *